United States Patent [19]

Kern

[11] Patent Number: 5,631,276
[45] Date of Patent: May 20, 1997

[54] SYNERGISTIC COMPOSITIONS FOR CONTROLLING INSECTS AND ACARINA

[75] Inventor: Manfred Kern, Lörzweiler, Germany

[73] Assignee: Hoechst Schering AgrEvo GmbH, Berlin, Germany

[21] Appl. No.: 432,209

[22] PCT Filed: Nov. 9, 1993

[86] PCT No.: PCT/EP93/03128

§ 371 Date: Jul. 3, 1995

§ 102(e) Date: Jul. 3, 1995

[87] PCT Pub. No.: WO94/10846

PCT Pub. Date: May 26, 1994

[30] Foreign Application Priority Data

Nov. 13, 1992 [DE] Germany .................. 42 38 311.0

[51] Int. Cl.$^6$ .................. A01N 43/02; A01N 43/22; A01N 63/00; A01N 63/04
[52] U.S. Cl. .................. 514/431; 424/93.5
[58] Field of Search .................. 514/431; 424/93.5

[56] References Cited

U.S. PATENT DOCUMENTS 4,271,181  6/1981  Eastburg ............................. 424/276
4,751,082  6/1988  Schaerffenberg et al. ............ 424/93

FOREIGN PATENT DOCUMENTS

WO92/20229  11/1992  WIPO.

OTHER PUBLICATIONS

Anderson, T.R., et al., "Compatibility of Beauveria bassiana Isolates with Insecticide Formulations Used in Colorado Potato Beetle (Coleoptera: Chrysomelidae) Control" J. Econ. Entomol. 76: 1437–1441, (1983).

Boas, Artemesia Meneses Vilas, "Efeito de Inseticidas en Subdoses sobre o Fungo Beauveria bassiana E Sobre as Brocas da Cana–de Acucar" Arq. Biol. Techol. 34(2), 287–302, Jun. 1991.

Olmert, I, et al., "Sensitivity of the Entolopathogenic Fungi, Beauveria bassiana, Verticillium lecanii, and Verticillium sp. to Fungicides and Insecticides" Entomological Society of America, 3: 33–38, (Feb. 15, 1974).

Prior, C., et al., "Infectivity of Oil and Water Formulations of Beauveria bassiana (Deuteromycotina: Hyphomycetes) to the Cocoa Weevil Pest Pantorhytes plutus (Coleoptera: Cruculionidae)" J. Invertebrate Pathology, 52:66–72, (1988).

Primary Examiner—Allen J. Robinson
Attorney, Agent, or Firm—Curtis, Morris & Safford P.C.

[57] ABSTRACT

The present invention relates to insecticidal and acaricidal compositions which comprise an effective content of endosulfan (A)

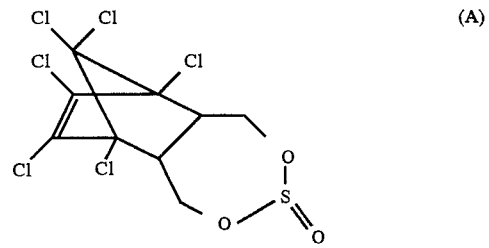

in combination with the entomopathogenic fungus *Beauveria bassi

SYNERGISTIC COMPOSITIONS FOR CONTROLLING INSECTS AND ACARINA

DESCRIPTION

This application is a 371 of PCT/EP93/03128 filed Nov. 9, 1993.

Frequently, the potency of biological pesticides is insufficient to protect crops of useful plants adequately against pests. This is why, to date, preference has been given to chemical insecticides. Integrated crop protection is intended to minimize the use of chemicals without having to accept reduced yields. The work of Soper et al. (1974, Environmental Entomology, 3, 560–562) shows that the growth of entomopathogenic fungi is inhibited by the simultaneous use of insecticides. Even though this depends on the type and the amount of the agent used, it can be seen from the data that endosulfan has a powerful adverse effect on the growth of the fungi. Filho et al. (1987, Biologico, 53, 7–12, 69–70) also report that the growth of *Beauveria bassiana* is inhibited by a range of insecticides, inter alia endosulfan.

Surprisingly, it has now been found that the compound endosulfan and spores or particles of the entomopathogenic fungus *Beauveria bassiana*, when used together, show an exceedingly good activity against a broad spectrum of different insects and Acarina.

The present invention relates to insecticidal and acaricidal compositions which comprise an effective amount of endosulfan (A)

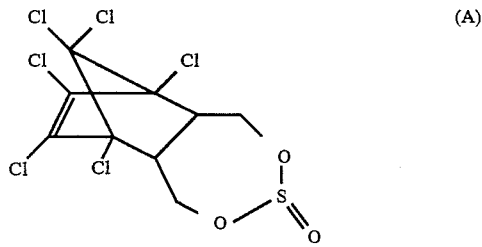

(A)

in combination with the entomopathogenic fungus *Beauveria bassiana* (B).

The compound endosulfan is well known from the literature and is prepared and marketed by Hoechst AG (Frankfurt, Germany) for example in the form of Thiodan. The fungus *Beauveria bassiana* has been described by Bassi, A. (1836, C.R. Acad. Sci. Paris 2, 434 to 436), Domsch, V. H. et al. (190, Compendium of Soil Fungi 1, 136 to 139) and Samson, R. A. et al. (1988, Atlas of Entomopathogenic Fungi, Springer-Verlag, Berlin) and is available from Mycotech (Butte, Mont., USA), from Hoechst AG and from Fermone Corp. (Phoenix, Ariz., USA). In the text which follows, the term active substance is also used for each of the two components A or B.

The mixing ratios of the two components can vary within wide limits. They depend, in particular, on the mixing partner employed, on the development stage of the pests and on the climatic conditions.

The active substance combinations according to the invention can exist either in the form of mixed formulations of the two components, which are then diluted with water in the customary manner or applied as granules, or they can be prepared as so-called tank mixes by jointly diluting the components, which are formulated separately, with water.

The invention also relates to compositions which contain the two components A and B in addition to suitable formulation auxiliaries.

The components can be formulated in a variety of ways, depending on the given biological and/or chemico-physical parameters. Suitable formulation options are, for example: yeast formulations, starch formulations, wettable powders (WP), emulsifiable concentrates (EC), aqueous solutions (SL), emulsions (EW) such as oil-in-water and water-in-oil emulsions, sprayable solutions or emulsions, dispersions on an oil or water basis, suspoemulsions, dusts (DP), seed-dressing agents, granules for soil application or broadcasting or water-dispersible granules (WG) and (WEG), ULV formulations, microcapsules, baits (substrates) or waxes.

Particularly interesting are oil-in-water and water-in-oil emulsions, wettable powders or granules.

These individual formulation types are known in principle and are described, for example, in: Winnacker-Küchler, "Chemische Technologie [Chemical Technology]", Volume 7, C. Hauser Verlag Munich, 4th Ed., 1986; van Valkenburg, "Pesticides Formulations", Marcel Dekker N.Y., 2nd Ed. 1972–73; K. Martens, "Spray Drying Handbook", 3rd Ed., G. Goodwin Ltd. London.

The formulation auxiliaries required, such as inert materials, surfactants, solvents and other additives, are also known and are described, for example, in: Watkins, "Handbook of Insecticide Dust Diluents and Carriers", 2nd Ed., Darland Books, Caldwell N.J.; H. v. Olphen, "Introduction to Clay Colloid Chemistry", 2nd Ed., J. Wiley & Sons, N.Y.; Marsden, "Solvents Guide", 2nd Ed., Interscience, N.Y. 1950; McCutcheon's "Detergents and Emulsifiers Annual", MC Publ. Corp. Ridgewood N.J.; Sisley and Wood, "Encyclopedia of Surface Active Agents", Chem. Publ. Co. Inc., N.Y. 1964; Schönfeldt, "Grenzflächenaktive Äthlenoxidaddukte [Surface-active Ethylene Oxide Adducts]", Wiss. Verlagsgesell., Stuttgart 1976; Winnacker-Küchler, "Chemische Technologie [Chemical Technology]", Volume 7, C. Hauser Verlag Munich, 4th Ed. 1986.

Combinations with other pesticidally active substances, such as selective herbicides, specific fungicides or insecticides and fertilizers and/or growth regulators may also be prepared on the basis of these formulations, for example in the form of a ready mix or as a tank mix.

Wettable powders are preparations which are uniformly dispersible in water and which, besides the active substance, also contain wetting agents, for example polyoxethylated alkylphenols, polyoxethylated fatty alcohols or fatty amines, alkanesulfonates or alkylbenzenesulfonates, and dispersing agents, for example sodium ligninsulfonate, sodium 2,2'-dinaphthylmethane-6,6'-disulfonate, sodium dibutylnaphthalenesulfonate, or else sodium oleylmethyltaurinate, in addition to a diluent or inert substance.

Emulsifiable concentrates are prepared by dissolving the active substance in an organic solvent, for example butanol, cyclohexanone, dimethylformamide, xylene or else higher-boiling aromatic compounds or hydrocarbons, with the addition of one or more emulsifiers. Examples of emulsifiers which can be used are: calcium salts of an alkylarylsulfonic acid, such as calcium dodecylbenzenesulfonate, or non-ionic emulsifiers, such as fatty acid polyglycol esters, alkylaryl polyglycol ethers, fatty alcohol polyglycol ethers, propylene oxide/ethylene oxide condensation products, alkyl polyethers, sorbitan fatty acid esters, polyoxyethylene sorbitan fatty acid esters or polyoxyethylene sorbitol esters.

Dusts can be obtained by grinding the active substance with finely divided solid substances, for example talc or natural clays, such as kaolin, bentonite, pyrophyllite, or diatomaceous earth.

Granules can be produced either by spraying the active substance onto adsorptive, granulated inert material or by applying active substance concentrates onto the surface of carriers, such as sand, kaolinites or granulated inert material, by means of binders, for example polyvinyl alcohol, sodium polyacrylate or, alternatively, mineral oils. Suitable active substances can also be granulated in the manner which is conventional for the production of fertilizer granules, if desired in a mixture with fertilizers.

As a rule, the agrochemical preparations contain 0.1 to 99 percent by weight, in particular 2 to 95% by weight, of the two components A and B. The formulations can contain different concentrations of the active substances A and B.

The concentration of active substance in wettable powders is, for example, about 10 to 95% by weight; the remainder to 100% by weight is composed of conventional formulation components. In the case of emulsifiable concentrates, the concentration of active substance can be about 1 to 85% by weight, preferably 5 to 80% by weight. Formulations in the form of dusts contain about 1 to 25% by weight, preferably 5 to 20% by weight, of active substance, sprayable solutions about 0.2 to 25% by weight, preferably 2 to 20% by weight, of active substance. In the case of granules, for example water-dispersible granules, the active substance content depends partly on whether the active compound is in liquid or solid form and on which granulation auxiliaries and fillers are used. As a rule, water-dispersible granules contain between 5 and 90% by weight, granules for broadcasting between 1 and 50%, preferably between 2 and 25%, of active substance.

In addition, the active substance formulations mentioned contain, if appropriate, the adhesives, wetting agents, dispersants, emulsifiers, penetrants, solvents, fillers or carriers which are conventional in each case.

For use, the formulations, which are present in commercially available form, are diluted, if appropriate, in a customary manner, for example using water in the case of wettable powders, emulsifiable concentrates, dispersions and water-dispersible granules. Preparations in the form of dusts or granules for soil application or for broadcasting and sprayable solutions are usually not further diluted with other inert substances before use.

The component B can be formulated for example as described by Prior, C. et al. in the Journal of Invertebrate Pathology 52, 66 to 72 (1988).

The term "coated material" denotes a formulation described in Patent Application WO 92/20229 (1992, Korea Res. Inst. Chem. Technology). Granules which are described in U.S. Pat. No. 5,120,542 (1992, ICI) are also of particular interest.

The quantity of the mixture required varies with the external conditions, such as, for example, temperature, humidity and the like.

The combination of the two components endosulfan (A) and the fungus (B) is well tolerated by plants, has a favorable toxicity to warm-blooded animals and can be used for controlling animal pests found in agriculture, in particular insects and arachnids.

The synergistic mixture of the two components is active against normally sensitive and resistant species and against certain stages of development. The compositions according to the invention have an outstanding insecticidal activity against a broad spectrum of economically important pests. Some representatives of pests which can be controlled by the compositions according to the invention may be mentioned individually by way of example, but this is not intended as a limitation to certain species.

Order of the Isopoda, for example, *Oniscus asellus, Armadium vulgare* and *Porcellio scaber*. From the order of the Diplopoda, for example, *Blaniulus guttulatus*. From the order of the Chilopoda, for example, *Geophilus carpophagus* and Scutigera spec. From the order of the Symphyla, for example, *Scutigerella immaculata*. From the order of the Thysanura, for example, *Lepisma saccharina*. From the order of the Collembola, for example, *Onychiurus armatus*. From the order of the Orthoptera, for example, *Blatta orientalis, Periplaneta americana, Leucophaea maderae,*
*Blattella germanica, Acheta domesticus,* Gryllotalpa spp., *Locusta migratoria migratorioides, Melanoplus differentialis* and *Schistocerca gregaria*. From the order of the Dermaptera, for example, *Forficula auricularia*. From the order of the Isoptera, for example, Reculitermes spp. From the order of the Anoplura, for example, *Phylloxera vastatrix,* Pemphigus spp., *Pediculus humanus corporis,* Haematopinus spp. and Linognathus spp.

From the order of the Mallophaga, for example, Trichodectes spp. and Damalinea spp. From the order of the Thysanoptera, for example, *Hercinothrips femoralis* and *Thrips tabaci*. From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Scotinophora coarctata, Drosicha mangiferae, Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.

From the order of the Heteroptera, for example, Lygus spp., *Nezara viridula, Drasicha mangiferae* and Euschistus spp.

From the order of the Lepidoptera, for example, *Pectinophora gossypiella, Bupalus piniarius, Cheimatobia brumata, Lithocolletis blancardella, Hyponomeuta padella,* Plutella maculipennis, Malacosoma neustria, Euproctis chrysorrhoea,* Lymantria spp., *Diathrea sacharalis, Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Ostrinia spp., *Perileucoptera coffeella,* Pieris spp., Chilo spp., *Pyrausta nubilalis, Ephestia kuehniella, Galleria mellonella, Tineola bissellleila, Tinea pellionella, Hofmannophila pseudospretella, Cacoecia podana, Capua reticulana, Choristoneura fumiferana, Clysia ambiguella, Homona magnanima, Tortfix viridana,* Dendrolimus spp., *Laspeyresia pomonella*.

From the order of the Coleoptera, for example, *Anobium punctatum, Hypothemenus hampei, Pityogenes chalcographus, Cyrtomon luridus, Xyloterus lineatus, Ips typographus, Rhizopertha dominica, Bruchidius obtectus, Acenthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Sitona lineatus, Cosmopolites sordidus, Ceuthorrhynchus assimilis, Hypera postica, Dermestes spp.,* Trogoderma spp., Anthrenus spp., Attagenus spp., Lyctus spp., *Meligethes aeneus,* Ptinus spp., *Niptus hololeucus, Gibbium psylloides,* Tribolium spp., *Brontispa longissima, Tenebrio molitor,* Agriotes spp., Conoderus spp., *Melolontha melolontha, Sphenophorus levis, Amphimallon solstitialis* and *Costelytra zealandica*.

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hypobosca spp., *Glossina morsitans,* Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa*.

From the order of the Siphonaptera, for example, *Xenopsylla cheopis* and *Ceratophyllus* spp. From the order of the Arachnida, for example, *Scorpio maurus* and *Latrodectus mactans*. From the order of the Acarina, for example, *Acarus siro*, *Argas* spp., *Ornithodoros* spp., *Dermanyssus gallinae*, *Eriophyes ribis*, *Phyllocoptruta oleivora*, *Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa*, *Panonychus* spp. and *Tetranychus* spp.

The combination according to the invention, of endosulfan ($\alpha$- and $\beta$-sulfates) and *Beauveria bassiana* is particularly suitable for controlling sensitive and resistant *Heliothis* spp., *Anthonomus* spp., *Hypothememus hampei*, *Spodoptera* spp., *Nephotettix* spp., *Trichoplusia* spp. and *Leptinotara decemlineata* and other feeding and sucking insects or spider mites (whitefly, Lepidoptera larvae).

The active substance combinations according to the invention allow an insecticidal and acaricidal activity to be achieved which exceeds that to be expected on the basis of the activity of the individual components. These increases in activity allow the application rates of the individual active substances to be reduced considerably. The combination of the active substances can also improve their long-term activity or cause an acceleration of the rate of activity. Such properties are of considerable advantage to the user for controlling insects in practice. They allow insects to be controlled more economically and more rapidly, with less labor and over a prolonged period, which means that better harvests are possible in a population of crop plants.

A further increase in activity can be achieved by using so-called feeding attractants or phagostimulants, such as, for example, Konsume (from Pharmone), ATPlus, yeast, starch, Stirrup (from Atochem, North America Inc., USA) and Coax.

Even though the compositions according to the invention have an outstanding insecticidal and acaricidal activity, the crop plant is not harmed at all. This is why the compositions are particularly suitable in cotton, soya bean and rice crops. They are also suitable for controlling pests in coffee, fruit, flour and vegetable production, or else in viticulture.

The following examples are intended to illustrate the invention without imposing any restriction:

A. BIOLOGICAL EXAMPLES

In all cases, a differentiation was made between the calculated and the found degree of effectiveness of the combinations.

If the actual damage exceeds the damage expected by way of calculation, then the activity of the combination is superadditive, i.e. there is a synergistic effect. The active substance combinations according to the invention have an insecticidal activity which exceeds that to be expected on the basis of the observed activities of the individual components when used by themselves. This means that the active substance combinations are synergistic.

EXAMPLE 1

*Spodoptera littoralis*

Egyptian cotton leaf worm larvae (*Spodoptera littoralis* L 3) together with suitable feed were sprayed with the components endosulfan (A) and *B. bassiana* (B) or mixtures of these. The effect of the individual components and of the mixtures of the individual components was assessed 7 days after keeping the test material at 25° C. and a relative atmospheric humidity of 90%.

| Active substance/component | Active substance in ppm | % mortality |
|---|---|---|
| Endosulfan (A) | 63 | 60 |
| | 31 | 50 |
| | 16 | 30 |
| | 8 | 0 |
| *Beauveria bassiana* (B) | $1.0 \cdot 10^{10}$ Conidia/ha | 0 |

| | (A) | + | (B) | By calculation | In the experiment |
|---|---|---|---|---|---|
| (A) + (B) | 63 | + | $1.0 \cdot 10^{10}$ | 60 | 80 |
| | 31 | + | $1.0 \cdot 10^{10}$ | 50 | 60 |
| | 16 | + | $1.0 \cdot 10^{10}$ | 30 | 60 |
| | 8 | + | $1.0 \cdot 10^{10}$ | 0 | 40 |

EXAMPLE 2

*Spodoptera littoralis* (Pyrethroid-resistant)

Pyrethroid-resistant Egyptian cotton leaf worm larvae (*Spodoptera littoralis* L 3) together with suitable feed were sprayed with the active substances or their mixtures. The effect of the individual components and of the mixtures of the individual components was assessed 7 days after keeping the test material at 25° C. and a relative atmospheric humidity of 90%.

| Active substance/component | Active substance in ppm | mortality |
|---|---|---|
| Endosulfan (A) | 125 | 100 |
| | 63 | 70 |
| | 31 | 30 |
| | 16 | 10 |
| | 8 | 0 |
| | 4 | 0 |
| | 2 | 0 |
| | 1 | 0 |
| *Beauveria bassiana* (B) | $1.0 \cdot 10^{10}$ Conidia/ha | 0 |

| | (A) | + | (B) | By calculation | In the experiment |
|---|---|---|---|---|---|
| (A) + (B) | 125 | + | $1.0 \cdot 10^{10}$ | 100 | 100 |
| | 63 | + | $1.0 \cdot 10^{10}$ | 70 | 80 |
| | 31 | + | $1.0 \cdot 10^{10}$ | 30 | 50 |
| | 16 | + | $1.0 \cdot 10^{10}$ | 10 | 40 |
| | 8 | + | $1.0 \cdot 10^{10}$ | 0 | 20 |
| | 4 | + | $1.0 \cdot 10^{10}$ | 0 | 0 |
| | 2 | + | $1.0 \cdot 10^{10}$ | 0 | 0 |
| | 1 | + | $1.0 \cdot 10^{10}$ | 0 | 0 |

EXAMPLE 3

*Heliothis virescens*

Cotton bollworm larvae (*Hellothis virescens*, L 2) together with suitable feed were sprayed with the active substances or their mixtures. The effect of the individual components and of the mixtures of the individual components was assessed 7 days after keeping the test material at 25° C. and a relative atmospheric humidity of 90%.

| Active substance/component | Active substance in ppm | % mortality |
|---|---|---|
| Endosulfan (A) | 125 | 70 |
| | 63 | 30 |
| | 31 | 30 |
| | 16 | 20 |
| | 8 | 10 |
| | 4 | 0 |
| | 2 | 0 |
| | 1 | 0 |
| | 0.5 | 0 |
| Beauveria bassiana (B) | $1.5 \cdot 10^{10}$ Conidia/ha | 16 |

| | (A) | + | (B) | By calculation | In the experiment |
|---|---|---|---|---|---|
| (A) + (B) | 125 | + | $1.5 \cdot 10^{10}$ | 86 | 90 |
| | 63 | + | $1.5 \cdot 10^{10}$ | 46 | 80 |
| | 31 | + | $1.5 \cdot 10^{10}$ | 46 | 60 |
| | 16 | + | $1.5 \cdot 10^{10}$ | 36 | 50 |
| | 8 | + | $1.5 \cdot 10^{10}$ | 26 | 60 |
| | 4 | + | $1.5 \cdot 10^{10}$ | 16 | 40 |
| | 2 | + | $1.5 \cdot 10^{10}$ | 16 | 30 |
| | 1 | + | $1.5 \cdot 10^{10}$ | 16 | 30 |
| | 0.5 | + | $1.5 \cdot 10^{10}$ | 16 | 20 |

EXAMPLE 4

Hypothenemus hampei

On a paper filter base (Petri dish), adult specimens of the coffee berry borer (*Hypothenemus hampei*) together with a coffee berry (feed) were sprayed with the active substances or their mixtures. The effect of the individual components and of the mixtures of the individual components was assessed 14 days after keeping the test material at 25° C. and a relative atmospheric humidity of 90%.

| Active substance/component | Active substance in ppm | % mortality |
|---|---|---|
| Endosulfan (A) | 0.25 | 80 |
| | 0.125 | 50 |
| | 0.063 | 50 |
| | 0.031 | 20 |
| | 0.016 | 20 |
| | 0.008 | 0 |
| | 0.004 | 0 |
| | 0.002 | 0 |
| | 0.001 | 0 |
| Beauveria bassiana (B) | $2 \cdot 10^{13}$ Conidia/ha | 35 |

| | (A) | + | (B) | By calculation | In the experiment |
|---|---|---|---|---|---|
| (A) + (B) | 0.25 | + | $2 \cdot 10^{13}$ | 100 | 100 |
| | 0.125 | + | $2 \cdot 10^{13}$ | 85 | 100 |
| | 0.063 | + | $2 \cdot 10^{13}$ | 85 | 100 |
| | 0.031 | + | $2 \cdot 10^{13}$ | 55 | 80 |
| | 0.016 | + | $2 \cdot 10^{13}$ | 55 | 70 |
| | 0.008 | + | $2 \cdot 10^{13}$ | 35 | 70 |
| | 0.004 | + | $2 \cdot 10^{13}$ | 35 | 70 |
| | 0.002 | + | $2 \cdot 10^{13}$ | 35 | 70 |
| | 0.001 | + | $2 \cdot 10^{13}$ | 35 | 60 |

EXAMPLE 5

Anthonomus grandis

Adult specimens of the cotton bollweevil (*Anthonomus grandis*) together with suitable feed (synthetic feed) were sprayed with the active substances or their mixtures. The effect of the individual components and of the mixtures of the individual components was assessed 11 days after keeping the test material at 25° C. and a relative atmospheric humidity of 90%.

| Active substance/component | Active substance in ppm | % mortality |
|---|---|---|
| Endosulfan (A) | 63 | 100 |
| | 31 | 83 |
| | 16 | 100 |
| | 8 | 50 |
| | 4 | 0 |
| | 2 | 17 |
| | 1 | 0 |
| Beauveria bassiana (B) | $2.0 \cdot 10^{13}$ Conidia/ha | 40 |

| | (A) | + | (B) | By calculation | In the experiment |
|---|---|---|---|---|---|
| (A) + (B) | 63 | + | $2 \cdot 10^{13}$ | 100 | 100 |
| | 31 | + | $2 \cdot 10^{13}$ | 100 | 100 |
| | 16 | + | $2 \cdot 10^{13}$ | 100 | 100 |
| | 8 | + | $2 \cdot 10^{13}$ | 90 | 100 |
| | 4 | + | $2 \cdot 10^{13}$ | 40 | 100 |
| | 2 | + | $2 \cdot 10^{13}$ | 57 | 84 |
| | 1 | + | $2 \cdot 10^{13}$ | 40 | 50 |

EXAMPLE 6

Leptinotarsa decemlineata

Adult specimens of the colorado beetle (*Leptinotarsa decemlineata*) together with suitable feed (potato leaves) were sprayed with the active substances or their mixtures. The effect of the individual components and of the mixtures of the individual components was assessed 14 days after keeping the test material at 25° C. and a relative atmospheric humidity of 90%.

| Active substance/component | Active substance in ppm | % mortality |
|---|---|---|
| Endosulfan (A) | 500 | 100 |
| | 250 | 100 |
| | 125 | 80 |
| | 63 | 90 |
| | 31 | 80 |
| | 16 | 80 |
| | 8 | 40 |
| | 4 | 40 |
| | 2 | 10 |
| | 1 | 0 |
| Beauveria bassiana (B) | $1.7 \cdot 10^{10}$ Conidia/ha | 22 |

| | (A) | + | (B) | By calculation | In the experiment |
|---|---|---|---|---|---|
| (A) + (B) | 500 | + | $2 \cdot 10^{10}$ | 100 | 100 |
| | 250 | + | $2 \cdot 10^{10}$ | 100 | 100 |
| | 125 | + | $2 \cdot 10^{10}$ | 100 | 100 |
| | 63 | + | $2 \cdot 10^{10}$ | 100 | 100 |
| | 31 | + | $2 \cdot 10^{10}$ | 100 | 100 |
| | 16 | + | $2 \cdot 10^{10}$ | 100 | 100 |
| | 8 | + | $2 \cdot 10^{10}$ | 62 | 80 |
| | 4 | + | $2 \cdot 10^{10}$ | 62 | 80 |
| | 2 | + | $2 \cdot 10^{10}$ | 32 | 80 |
| | 1 | + | $2 \cdot 10^{10}$ | 22 | 60 |

EXAMPLE 7

Trialeurodes vaporariorum

Bean leaves (*Phaseolus vulgaris*) were sprayed with active substances or mixtures (endosulfan, *B. bassiana*) at various concentrations and subsequently infested with 50 adult specimens of whitefly (*Trialeurodes vaporariorum*). The effect of the individual components and of the mixtures of the individual components was assessed 8 days after keeping the test material at 25° C. and a relative atmospheric humidity of 80%.

| Active substance/ component | Active substance in ppm | % mortality |
|---|---|---|
| Endosulfan (A) | 125 | 100 |
| | 63 | 84 |
| | 31 | 50 |
| | 16 | 36 |
| | 8 | 24 |
| | 4 | 0 |
| | 2 | 0 |
| | 1 | 0 |
| | 0.5 | 0 |
| | 0.25 | 0 |
| *Beauveria bassiana* (B) | $2.24 \cdot 10^{10}$ Conidia/ha | 36 |

| | (A) | + | (B) | By calculation | In the experiment |
|---|---|---|---|---|---|
| (A) + (B) | 125 | + | $2.24 \cdot 10^{10}$ | 100 | 100 |
| | 63 | + | $2.24 \cdot 10^{10}$ | 100 | 100 |
| | 31 | + | $2.24 \cdot 10^{10}$ | 86 | 100 |
| | 16 | + | $2.24 \cdot 10^{10}$ | 52 | 100 |
| | 8 | + | $2.24 \cdot 10^{10}$ | 44 | 100 |
| | 4 | + | $2.24 \cdot 10^{10}$ | 36 | 72 |
| | 2 | + | $2.24 \cdot 10^{10}$ | 36 | 72 |
| | 1 | + | $2.24 \cdot 10^{10}$ | 36 | 40 |
| | 0.5 | + | $2.24 \cdot 10^{10}$ | 36 | 30 |
| | 0.25 | + | $2.24 \cdot 10^{10}$ | 36 | 32 |

I claim:

1. An insecticidal and/or acaricidal composition which comprises synergistic effective amounts of endosulfan (A) and *Beauveria bassiana* (B).

2. The composition as claimed in claim 1, which comprises 1 to 99% by weight of endosulfan and *Beauveria bassiana*.

3. The composition as claimed in claim 1, which is formulated in a conventional crop protection product formulation selected from the group consisting of wettable powders, emulsifiable concentrates, aqueous solutions, emulsions, sprayable solutions, dispersions on an oil or water basis, suspoemulsions, dusts, seed-dressing agents, granules for soil application or for broadcasting, coated material, water-dispersible granules, water-emulsifiable granules, ULV formulations, microcapsules, silica gels, polymer gels, saccharomyces, bacteria and waxes.

4. The composition as claimed in claim 1, further comprising a formulation auxiliary selected from the group consisting of adhesives, wetting agents, dispersants, emulsifiers, penetrants, solvents, fillers, surfactants and carriers.

5. A method of controlling insect pests or Acarina, which comprises applying a synergistic effective amount of the composition as claimed in claim 1 to the plants, areas or substrates infested with the insect pests or Acarina.

6. The method as claimed in claim 5, wherein the crop plants are vegetables or ornamentals grown under glass.

7. The method as claimed in claim 5, wherein the crop is cotton, soya beans, rice or coffee.

8. A method of controlling insect pests or Acarina, which comprises applying a synergistic effective amount of the composition as claimed in claim 1 to the insect pests or Acarina.

\* \* \* \* \*